(12) United States Patent
Kobushi et al.

(10) Patent No.: US 8,003,210 B2
(45) Date of Patent: Aug. 23, 2011

(54) PROCESS FOR PRODUCING WATER-ABSORBING RESIN PARTICLES, WATER-ABSORBING RESIN PARTICLES MADE BY THE PROCESS, AND ABSORBENT MATERIALS AND ABSORBENT ARTICLES MADE BY USING THE PARTICLES

(75) Inventors: Hiromu Kobushi, Himeji (JP); Masayoshi Handa, Himeji (JP); Yasuhiro Nawata, Himeji (JP)

(73) Assignee: Sumitomo Seika Chemicals Co., Ltd., Hyogo (JP)

( * ) Notice: Subject to any disclaimer, the term of this patent is extended or adjusted under 35 U.S.C. 154(b) by 289 days.

(21) Appl. No.: 11/914,506

(22) PCT Filed: May 10, 2006

(86) PCT No.: PCT/JP2006/309406
§ 371 (c)(1),
(2), (4) Date: Nov. 15, 2007

(87) PCT Pub. No.: WO2006/123561
PCT Pub. Date: Nov. 23, 2006

(65) Prior Publication Data
US 2008/0280154 A1 Nov. 13, 2008

(30) Foreign Application Priority Data
May 16, 2005 (JP) ................................. 2005-142700

(51) Int. Cl.
*B32B 5/16* (2006.01)
*C08G 65/30* (2006.01)
*C08G 65/331* (2006.01)
(52) U.S. Cl. ........ 428/402; 428/327; 502/402; 526/930; 528/425
(58) Field of Classification Search .......... 428/402–407, 428/327; 502/402; 526/930; 528/425
See application file for complete search history.

(56) References Cited

U.S. PATENT DOCUMENTS
4,666,975 A * 5/1987 Yamasaki et al. ............. 524/733
4,806,578 A * 2/1989 Kobayashi et al. ........... 523/402
(Continued)

FOREIGN PATENT DOCUMENTS
EP 0533192 A1 3/1993
(Continued)

OTHER PUBLICATIONS
Online machine translation of JP 07-088,171, 1995.*
(Continued)

*Primary Examiner* — Hoa Le
(74) *Attorney, Agent, or Firm* — Westerman, Hattori, Daniels & Adrian, LLP

(57) ABSTRACT

The present invention provides a process for producing water-absorbing resin particles which possess a high water retention capacity (absorbing capacity), a high water-absorbing capacity under pressure, and a high gel strength and a small amount of water-soluble substance and is favorably usable in sanitary materials; water-absorbing resin particles obtained by the process; and absorbent materials and absorbent articles made by using the particles. More specifically, the water-absorbing resin particles are produced by a process for producing water-absorbing resin particles, comprising a step of a post-crosslinking reaction by adding a post-crosslinking agent in at least two stages to a water-absorbing resin particle precursor obtained by polymerization of a water-soluble ethylenic unsaturated monomer to carry out the post-crosslinking reaction.

6 Claims, 2 Drawing Sheets

U.S. PATENT DOCUMENTS

| | | | |
|---|---|---|---|
| 5,976,696 A | 11/1999 | Collette et al. | |
| 2007/0141338 A1 * | 6/2007 | Ishizaki et al. | 428/402 |

FOREIGN PATENT DOCUMENTS

| EP | 0629411 A1 | 12/1994 |
|---|---|---|
| JP | 01-213307 A | 8/1989 |
| JP | 1213307 A | 8/1989 |
| JP | 03-195705 A | 8/1991 |
| JP | 03-197512 A | 8/1991 |
| JP | 3187512 A | 8/1991 |
| JP | 3195705 A | 8/1991 |
| JP | 7-26026 A | 1/1995 |
| JP | 788171 A | 4/1995 |
| JP | 2000-026510 A | 1/2000 |
| JP | 200026510 A | 1/2000 |
| JP | 2001-040014 A | 2/2001 |
| JP | 200140014 A | 2/2001 |

OTHER PUBLICATIONS

Notification of Transmittal of Translation of the International Preliminary Report on Patentability (Form PCT/IB/338) of International Application No. PCT/JP2006/309406 mailed Nov. 29, 2007 with Forms PCT/IB/373, PCT/ISA/237, and PCT/IB/326.

International Search Report of PCT/JP2006/309406, date of mailing Aug. 8, 2006.

Supplementary European Search Report date Sep. 30, 2010, issued in corresponding European Patent Application No. 06746220.0.

* cited by examiner

PROCESS FOR PRODUCING WATER-ABSORBING RESIN PARTICLES, WATER-ABSORBING RESIN PARTICLES MADE BY THE PROCESS, AND ABSORBENT MATERIALS AND ABSORBENT ARTICLES MADE BY USING THE PARTICLES

TECHNICAL FIELD

The present invention relates to a process for producing a water-absorbing resin particle. More particularly, the present invention relates to a process for producing a water-absorbing resin particle which possesses a high water retention capacity (absorbing capacity), a high water-absorbing capacity under pressure, and a high gel strength, and a small amount of water-soluble substance and is favorably usable in sanitary materials; a water-absorbing resin particle obtainable by the same process; and an absorbent material and an absorbent article made by using the particle.

BACKGROUND ART

A water-absorbing resin has hitherto been widely used in sanitary materials such as a paper diaper, a sanitary napkin etc., and industrial materials such as a water blocking material for a cable etc. A hydrolysate of a starch-acrylonitrile graft copolymer, a neutralized material of a starch-acrylic acid graft copolymer, a saponified material of a vinyl acetate-acrylic acid ester copolymer, a partially neutralized material of a polyacrylic acid and the like are known as the water-absorbing resin.

In recent years, in the sanitary materials such as a paper diaper, a sanitary napkin etc., the absorbent material tends to be thinned from a viewpoint of an amenity for use. Examples of reduction in a thickness of the absorbent material include a method for increasing a proportion of a water-absorbing resin in the absorbent material, a method for increasing the water retention capacity of the water-absorbing resin, and the like.

In the former method for increasing a proportion of the water-absorbing resin in an absorbent material, it becomes easy for water-absorbing resins to cause gel blocking to each other upon absorbing a body fluid. Therefore, the higher water-absorbing capacity under pressure of the water-absorbing resin is required in order to suppress the gel blocking between water-absorbing resins. However, in order to increase the water-absorbing capacity under pressure, it is generally necessary to increase a crosslinking density of the water-absorbing resin and, there is a problem that the water retention capacity of the water-absorbing resin decreases consequently.

In the latter method for increasing the water retention capacity of a water-absorbing resin, it is necessary to reduce a crosslinking density of the water-absorbing resin. Consequently, an uncrosslinked component is increased, and upon contacting with a liquid, a water-absorbing rate tends to decrease by making the lump state, and a gel strength decreases, and a slime matter (water-soluble substance) after absorbing the fluid, tends to be easily eluted. When the above water-absorbing resin is used as a diaper, this becomes cause for flow-back increase of a body fluid due to deficiency of a gel strength, a rash due to a water-soluble substance, and the amenity of a wearer is deteriorated.

As the technology for improving the above property in order to be favorably used in sanitary materials, the following technologies are known: a method for carrying out reverse phase suspension polymerization using a specific amount of a specific polymer protecting colloid and a specific surfactant (see Patent Literature 1), a method for performing reverse phase suspension polymerization in multi (two or more) steps (see Patent Literature 2), a method for performing reverse phase suspension polymerization in the presence of β-1,3-glucans to obtain a water-absorbing resin and then adding a crosslinking agent to the resultant water-absorbing resin to carry out a crosslinking reaction (see Patent Literature 3), a method for carrying out reverse phase suspension polymerization using a specific amount of a polymerization initiator persulfate (Patent Literature 4), a method for heating and mixing a water-absorbing resin precursor and a surface-crosslinking agent after the water-absorbing resin precursor is obtained by polymerizing it in an aqueous solution in the presence of phosphorous acid and/or a salt thereof (see Patent Literature 5), a method for mixing a water-absorbing resin with two or more kinds of crosslinking agents having different solubility parameters, and crosslinking the resin in a specific temperature range (see Patent Literature 6) and the like.

However, since these water-absorbing resins are such that, when the water retention capacity exceeds a certain value, a gel strength decreases, and a water-soluble substance increases, the performance of the absorbent material in which the above water-absorbing resins are used, is not sufficiently satisfactory.

Patent Literature 1: JP-A No. Hei 6-345819
Patent Literature 2: JP-A No. Hei 3-227301
Patent Literature 3: JP-A No. Hei 8-120013
Patent Literature 4: JP-A No. Hei 6-287233
Patent Literature 5: JP-A No. Hei 9-124710
Patent Literature 6: JP-A No. Hei 6-184320

DISCLOSURE OF THE INVENTION

Problems to be Solved by the Invention

An object of the present invention is to provide a process for producing a water-absorbing resin which possesses a high water retention capacity (absorbing capacity), a high water-absorbing capacity under pressure, and a high gel strength, and a small amount of water-soluble substance and is favorably usable in sanitary materials; a water-absorbing resin particle obtainable by the same process; and an absorbent material and an absorbent article made by using the particle.

Means to Solve the Problem

The present invention provides a process for producing a water-absorbing resin particle, comprising a step of adding a post-crosslinking agent in at least two stages to a water-absorbing resin particle precursor obtained by polymerizing a water-soluble ethylenic unsaturated monomer to carry out a post-crosslinking reaction.

The process of the present invention comprises, in particular, a first post-crosslinking reaction step of adding a post-crosslinking agent to a water-absorbing resin particle precursor having a water content of not less than 35% to carry out a post-crosslinking reaction; a water content adjustment step of reducing a water content of the post-crosslinked water-absorbing resin particle precursor to less than 35%; and a second post-crosslinking reaction step of adding a post-crosslinking agent to the post-crosslinked water-absorbing resin particle precursor having a reduced water content to carry out a post-crosslinking reaction.

Effect of the Invention

According to the present invention, a water-absorbing resin particle can be produced which possesses a high water retention capacity (absorbing capacity), a high water-absorbing capacity under pressure, and a high gel strength, and a small amount of water-soluble substance and is favorably usable in sanitary materials.

Further, an absorbent material and an absorbent article having the high water-absorbing capacity and the high water retention capacity can be obtained by using the water-absorbing resin particle obtained by the process of the present invention.

BEST MODE FOR CARRYING OUT THE INVENTION

Figure 1:
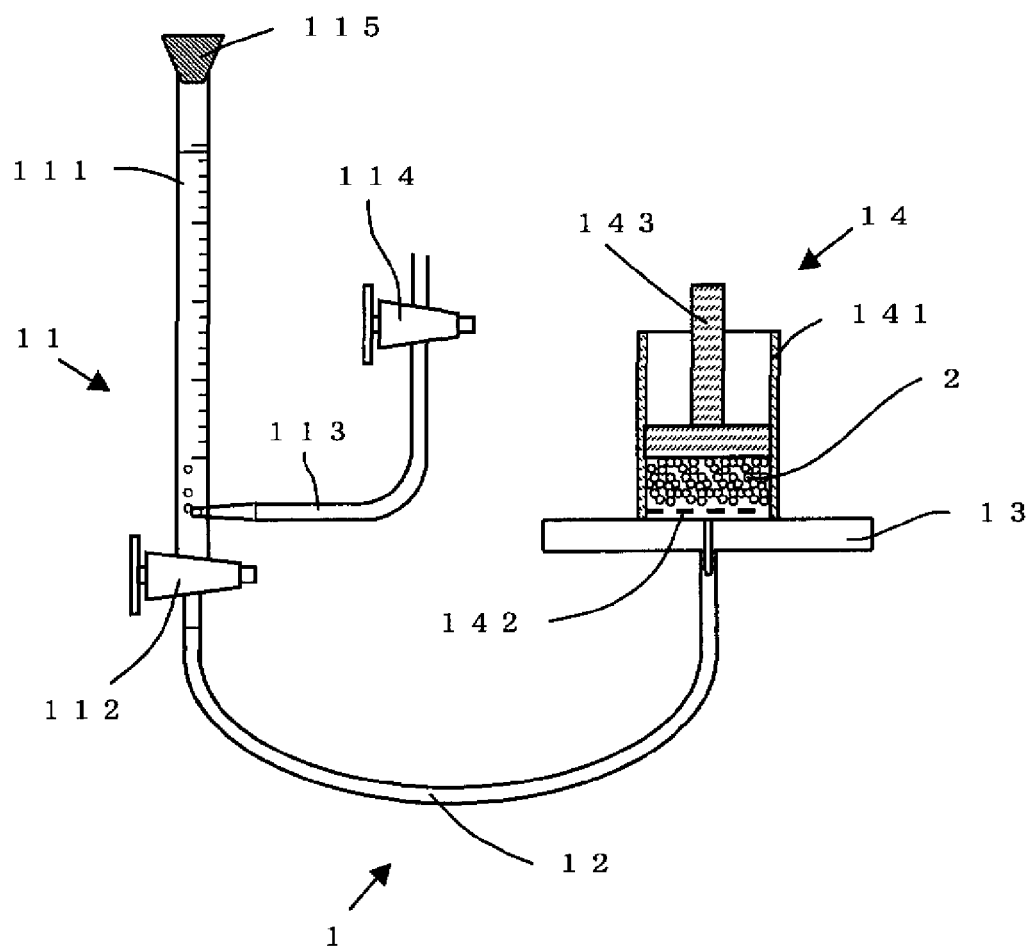
[FIG. 1] Schematic diagram of an apparatus for measuring the physiological saline absorbing capacity of water absorbing resin particles under the load of 4.14 kPa.

Examples of a process for producing a water-absorbing resin particle precursor used in the present invention include a method for polymerizing a water-soluble ethylenic unsaturated monomer. Examples of the polymerization method are not limited to, but include aqueous solution polymerization, emulsion polymerization, reverse phase suspension polymerization and the like, which are a typical polymerization method.

In the present description, explanation is made about the reverse phase suspension polymerization in more detail as one example of an embodiment. In the above method, a water-soluble ethylenic unsaturated monomer is subjected to reverse phase suspension polymerization in a water-in-oil system by using a water-soluble radical polymerizing initiator in a hydrocarbon medium in the presence of surfactant(s) and/or polymer protecting colloid(s).

Examples of the water-soluble ethylenic unsaturated monomer include (meth)acrylic acid ["(meth)acryl" means "acryl" and "methacryl"; the same hereinafter], 2-(meth) acrylamido-2-methylpropanesulfonic acid or an alkali metal salt thereof; a nonionic unsaturated monomer such as (meth) acrylamide, N,N-dimethyl(meth)acrylamide, 2-hydroxyethyl(meth)acrylate, N-methylol(meth)acrylamide etc.; and an amino group-containing unsaturated monomer such as diethylaminoethyl(meth)acrylate, diethylaminopropyl (meth)acrylate etc., or a quaternized compound thereof. They may be used alone, or may be used by mixing two or more kinds. Examples of an alkali metal in the alkali metal salt include lithium, sodium, potassium and the like.

Among the water-soluble ethylenic unsaturated monomer, preferable are (meth)acrylic acid or an alkali metal salt thereof, (meth)acrylamide and N,N-dimethylacrylamide, from a viewpoint of being industrially easily available. More preferable are (meth)acrylic acid or an alkali metal salt thereof, from a viewpoint of economical property.

The water-soluble ethylenic unsaturated monomer can be usually used as an aqueous solution. A concentration of the water-soluble ethylenic unsaturated monomer in an aqueous solution of the water-soluble ethylenic unsaturated monomer is preferably from 15% by mass to a saturated concentration.

In the case of the water-soluble ethylenic unsaturated monomer aqueous solution, when a water-soluble ethylenic unsaturated monomer to be used contains an acid group, the acid group may be neutralized with an alkali metal or the like. A degree of neutralization with an alkali metal is preferably in a range of 10 to 100 mole % of an acid group of a water-soluble ethylenic unsaturated monomer before the neutralization, from a viewpoint that an osmotic pressure of the resultant water-soluble resin is increased, a water absorption rate is increased, and a problem in safety and the like is not caused due to the presence of an excessive alkali metal. Examples of the alkali metal include lithium, sodium, potassium and the like. Among them, sodium and potassium are preferable, and sodium is more preferable.

Examples of the surfactant include nonionic surfactants such as sorbitan fatty acid esters, polyglycerin fatty acid esters, sucrose fatty acid esters, sorbitol fatty acid esters, polyoxyethylene alkyl phenyl ethers etc.; anionic surfactants such as fatty acid salts, alkylbenzenesulfonate salts, alkylmethyl taurate salts, polyoxyethylene alkyl phenyl ether sulfate ester salts, polyoxyethylene alkyl ether sulfonate salts, phosphonate esters of polyoxyethylene alkyl ethers, and the like. Among them, sorbitan fatty acid esters, polyglycerin fatty acid esters, phosphonate esters of polyoxyethylene alkyl ethers and sucrose fatty acid esters are preferable.

Examples of the polymeric protective colloid include ethylcellulose, ethylhydroxyethylcellulose, polyethylene oxide, maleic anhydride-modified polyethylene, maleic anhydride-modified polybutadiene, maleic anhydride-modified EPDM (ethylene-propylene-diene terpolymer) and the like.

An amount of the surfactant and/or the polymeric protective colloid is preferably 0.1 to 5 parts by mass, more preferably 0.2 to 3 parts by mass based on 100 parts by mass of an aqueous solution of the water-soluble ethylenic unsaturated monomer.

Examples of the water-soluble radical polymerization initiator include persulfate salts such as potassium persulfate, ammonium persulfate, sodium persulfate etc.; organic peroxides such as tert-butyl hydroperoxide, cumene hydroperoxide, benzoyl peroxide etc.; hydrogen peroxide; azo compounds such as 2,2'-azobis(2-amidinopropane) dihydrochloride etc. and the like. Among them, potassium persulfate, ammonium persulfate, sodium persulfate, benzoyl peroxide and 2,2'-azobis(2-amidinopropane) dihydrochloride are preferable from a viewpoint that they are easily available and have good storage stability. In addition, the water-soluble radical polymerization initiator may be used as a redox polymerization initiator together with a sulfite salt or the like.

It is preferable that an amount of the water-soluble radical polymerization initiator is usually 0.00005-0.01 mole per 1 mole of the water-soluble ethylenic unsaturated monomer from a viewpoint that a time period for a polymerization reaction is shortened and a rapid polymerization reaction is prevented.

In the present invention, the above polymerization reaction can be carried out in the presence of additive(s) such as a water-soluble chain transfer agent etc. from a viewpoint of controlling of an inner crosslinking density and a molecular weight. Example of such the additives include thiols, thiol acids, secondary alcohols, phosphorus compounds, lactic acid, aminocarboxylic acid metal chelating agents etc.

It is desirable that an amount of the above additives is 0.00001-0.05 mole, preferably 0.000015-0.02 mole, more preferably 0.0002-0.01 mole per 1 mole of a water-soluble ethylenic unsaturated monomer used. When the amount of an additive is less than 0.00001 mole, the effect of the additive does not tend to be sufficiently manifested. On the other hand, when the amount of an additive is more than 0.05 mole, a slime component (water-soluble component) after absorption of fluids tends to increase.

Examples of the hydrocarbon-based solvent include aliphatic hydrocarbons such as n-hexane, n-heptane etc.; alicyclic hydrocarbons such as cyclopentane, methylcyclopentane, cyclohexane, methylcyclohexane etc.; aromatic hydrocarbons such as benzene, toluene, xylene etc. Among them, n-hexane, n-heptane, and cyclohexane are preferable from a viewpoint of being industrially easily available, stable in quality and inexpensive.

Usually, an amount of the hydrocarbon-based solvent is preferably 50 to 600 parts by mass, more preferably 80 to 550 parts by mass based on 100 parts by mass of the water-soluble ethylenic unsaturated monomer from a viewpoint that heat of polymerization is removed and a polymerization temperature is easily controlled.

In the present invention, the polymerization reaction is preferably performed in the presence of an inner crosslinking agent. Examples of such the crosslinking agent include unsaturated polyesters obtained by reacting polyols of diols, triols etc. such as (polyethylene glycol ["(poly)" means both of the case where there is a prefix of "poly" and the case where there is no prefix of "poly"; the same hereinafter], (poly)propylene glycol, 1,4-butanediol, trimethylol propane, (poly)glycerin etc. with an unsaturated acid such as (meth)acrylic acid, maleic acid, fumaric acid etc.; bisacrylamides such as N,N'-methylenebisacrylamide etc.; di- or tri(meth)acrylic acid esters obtained by reacting polyepoxide with (meth)acrylic acid; di(meth)acrylic acid carbamyl esters obtained by reacting polyisocyanate such as tolylene diisocyanate, hexamethylene diisocyanate and the like with hydroxyethyl(meth)acrylate; compounds having two or more polymerizable unsaturated groups such as allylated starch, allylated cellulose, diallyl phthalate, N,N',N"-triallyl isocyanurate, divinylbenzene etc.; glycidyl compounds such as (poly)ethylene glycol diglycidyl ether, (polypropylene glycol diglycidyl ether, (poly)glycerin diglycidyl ether etc.; epihalohydrin compounds such as epichlorohydrin, epibromohydrin, α-methylepichlorohydrin etc.; compounds having two or more reactive functional groups such as isocyanate compounds such as 2,4-tolylene diisocyanate, hexamethylene diisocyanate etc.; oxetane compounds such as 3-methyl-3-oxetanemethanol, 3-ethyl-3-oxetanemethanol, 3-butyl-3-oxetanemethanol, 3-methyl-3-oxetanethanol, 3-ethyl-3-oxetanethanol, 3-butyl-3-oxetanethanol etc. They may be used alone, or may be used by mixing two or more kinds.

An amount of the inner crosslinking agent is preferably 0.000001-0.001 mole per 1 mole of a water-soluble ethylenic unsaturated monomer used, such that water solubility of the resultant polymer is controlled by a suitable crosslinking and exhibits sufficient water absorbency.

Although the reaction temperature of the polymerization reaction differs depending on the radical polymerization initiator used, the reaction temperature is preferably 20 to 110° C., more preferably 40 to 90° C. from a viewpoint of increasing productivity by shortening polymerization time with rapidly proceeding polymerization and smoothly performing the reaction by easily removing heat of polymerization. A reaction time is usually 0.5 to 4 hours.

Thus, the reverse phase suspension polymerization is carried out to obtain a water-absorbing resin particle precursor. The above water-soluble ethylenic unsaturated monomer is also added to the water-absorbing resin particle precursor obtained by the above reverse phase suspension polymerization, and polymerization may be carried out in multi steps (not less than two steps) to obtain a water-absorbing resin particle precursor.

The present invention comprises adding in at least two stages a post-crosslinking agent having two or more functional groups having reactivity against a carboxyl group to the resultant water-absorbing resin particle precursor to carry out post-crosslinking treatment by reacting it with the carboxyl group included in the water-absorbing resin particle precursor.

When a post-crosslinking agent is added to a water-absorbing resin particle precursor to carry out a crosslinking reaction, a crosslinking reaction is firstly carried out as a first crosslinking reaction step under the state that a water content of the water-absorbing resin particle precursor is high, and further subjected to a crosslinking reaction as a second crosslinking reaction step after lowering the water content to adjust it within a given range.

In addition, the water content of the present invention means a value by dividing a water amount in a water-containing water-absorbing resin particle precursor by a theoretical resin solid content, and converting this into a value expressed in percentage.

In the first post-crosslinking reaction step, a water content of the water-absorbing resin particle precursor is not less than 35%, more preferably 35-200%, most preferably 35-100%. When a water content of the water-absorbing resin particle precursor is less than 35%, there is a possibility that a gel strength of the resultant water-absorbing resin particle decreases, and a water-soluble substance increases.

After the first post-crosslinking reaction step, the post-crosslinking reaction is then accelerated, for example, by heating while removing a water of the water-absorbing resin particle precursor.

A second post-crosslinking reaction step is then carried out and, thereupon, a water content of the water-absorbing resin particle precursor is less than 35%, more preferably 15-33%, most preferably 20-30%. When a water content of the water-absorbing resin particle precursor is not less than 35%, there is a possibility that the water-absorbing capacity of the resultant water-absorbing resin particle under pressure decreases.

A difference in a water content of the water-absorbing resin particle precursor between the first and the second post-crosslinking reaction steps is not less than 5%, more preferably not less than 10%.

Examples of a method for adjusting a water content of the water-absorbing resin particle precursor in the above ranges, are not limited to, but include a method for heat-drying the water-absorbing resin particle precursor to a desired water content under atmospheric or reduced pressure, and a method for removing a water by azeotropic distillation in an inert organic solvent such as a hydrocarbon solvent and the like.

As the post-crosslinking agent, compounds having two or more of functional groups which may be reacted with a carboxyl group of the water-absorbing resin particle, can be used. Examples of the compound include polyols such as (polyethylene glycol, (polypropylene glycol, 1,4-butanediol, trimethylolpropane, (poly)glycerin etc.; glycidyl compounds such as (polyethylene glycol diglycidyl ether, (polypropylene glycol diglycidyl ether, (poly)glycerin diglycidyl ether etc.; epihalohydrin compounds such as epichlorohydrin, epibromohydrin, α-methylepichlorohydrin etc.; isocyanate compounds such as 2,4-tolylene diisocyanate, hexamethylene diisocyanate etc. Among them, from a viewpoint of a high reactivity and a rapid progress of the post-crosslinking reaction, the glycidyl compounds are preferably used. They may be used alone or may be used by mixing two or more kinds, and at least one kind of them is more preferably a glycidyl compound. The crosslinking agent may be used by dissolving it in water, organic solvent(s) and the like.

Although an amount of the post-crosslinking agent can not be unconditionally determined because the amount is different depending on a kind of the crosslinking agent, usually the amount in the first post-crosslinking reaction step is a proportion of 0.000005-0.002 mole, preferably 0.00001-0.001 mole, more preferably 0.00005-0.0005 mole, and the amount in the second post-crosslinking reaction step is a proportion of 0.000005-0.001 mole, preferably 0.00001-0.0005 mole, more preferably 0.00002-0.0003 mole per 1 mole of a total amount of the water-soluble ethylenic unsaturated monomer used for obtaining the water-absorbing resin particle precursor.

When an addition amount of the post-crosslinking agent in the first post-crosslinking reaction step is less than 0.000005 mole, there is a tendency that a crosslinking density of the water-absorbing resin can not be sufficiently increased and there is a possibility that a water-soluble substance increases. When the amount exceeds 0.002 mole, there is a tendency that the absorbing capacity decreases because of an excessive amount of the crosslinking agent.

On the other hand, when an addition amount of the post-crosslinking agent in the second post-crosslinking reaction step is less than 0.000005 mole, there is a tendency that a crosslinking density of the water-absorbing resin can not be increased and there is a possibility that the water absorbing capacity under pressure decreases. When the amount exceeds 0.001 mole, there is a tendency that not only the absorbing capacity decreases because of an excessive amount of the crosslinking agent, but also an unreacted crosslinking agent remains.

Examples of a method for adding the post-crosslinking agent to the water-absorbing resin particle precursor are not particularly limited to, but include a method for spraying a crosslinking agent solution to a resin particle by using a spray or the like, a method for adding a crosslinking agent in the state where the above water-absorbing resin particle precursor is dispersed in an inert organic solvent such as hydrocarbon solvents etc., and the like. In addition, if a water content of the water-absorbing resin particle precursor is within a predetermined range as described above, the post-crosslinking agents of the first and the second post-crosslinking reacting steps may be added while a water of the water-absorbing resin precursor is continuously removed by drying.

In addition, in the above post-crosslinking reaction step, it is preferable that an external energy such as heating etc. is provided in order to accelerate the crosslinking reaction. A required amount of energy can not be generally determined because the amount is different depending on a kind of the crosslinking agent, but, for example, when a glycidyl compound is used as the post-crosslinking agent, a temperature in the reaction system is retained at not lower than 50° C., preferably not lower than 70° C.

By further drying the water-absorbing resin particle precursor which has been post-crosslinked as described above, the water-absorbing resin particle of the present invention is obtained. The final water content (drying loss) of the water-absorbing resin particle is not more than 16%, more preferably not more than 12%, most preferably not more than 8%. When the water content of the water-absorbing resin particle is not less than 16%, there is a possibility that fluidity as a powder decreases.

Since the thus obtained water-absorbing resin particle of the present invention has the physiological saline retention capacity of 40-60 g/g, the physiological saline absorbing capacity under the load of 4.14 kPa of not less than 15 ml/g, a gel strength of not less than 500 Pa, a water-soluble substance of not more than 15% by mass, therefore, has a small amount of water-soluble substance, the high water retention capacity, the high water absorbing capacity under the load, and an excellent water absorbing rate, it can be suitably used in absorbent articles.

From a viewpoint that the higher physiological saline retention capacity can increase the absorbing capacity when used in absorbent articles, the physiological saline retention capacity is preferably 40-60 g/g, more preferably 45-55 g/g.

The physiological saline-absorbing capacity under the load of 4.14 kPa is preferably not less than 15 ml/g from a viewpoint that an advantage is possessed that a flow-back amount under application of a pressure on absorbent articles becomes smaller at the higher physiological saline-absorbing capacity when used in absorbent articles.

A gel strength is preferably not less than 500 Pa, more preferably not less than 1000 Pa from a viewpoint that, at a higher gel strength, a flow path of liquid is secured even under the load and a liquid diffusivity is enhanced when used as absorbent articles, by retaining a shape of a gel in absorbent articles after liquid absorption.

Since when used as absorbent articles, at a lower water-soluble substance, "slime" or "rash" due to a water-soluble substance is smaller, and the amenity upon having on the absorbent article is improved, the water-soluble substance is preferably not more than 15% by mass.

The absorbent material of the present invention comprises a water-absorbing resin particle and a hydrophilic fiber. Examples of the construction for the absorbent material include a mixing structure in which a water-absorbing resin particle and a hydrophilic fiber are uniformly blended; a sandwich structure in which a water-absorbing resin particle is held between lamellar hydrophilic fibers; and a structure in which a water-absorbing resin particle and a hydrophilic fiber are wrapped with a tissue paper; and the like, but the present invention is not limited only to such the examples. In addition, the absorbent material of the present invention may contain a synthetic fiber as a reinforcing material.

It is desirable that a content of the water-absorbing resin particle in the absorbent material is preferably 5-80% by mass, more preferably 10-70% by mass, further preferably 15-60% by mass. When a content of the water-absorbing resin particle is less than 5% by mass, there is a tendency that the absorbing capacity of the absorbent material decreases, leading to increase in liquid leakage and flow-back. When a content of the water-absorbing resin particle is more than 80% by mass, there is a tendency that the cost of the absorbent material increases and feeling of the absorbent material becomes hard.

Examples of the hydrophilic fiber include cellulose fibers obtained from timbers such as flocculent pulps, mechanical pulps, chemical pulps, semi-chemical pulps etc.; artificial cellulose fibers such as rayon, acetate fiber etc. and the like, and the present invention is not limited to such the examples. In addition, the hydrophilic fiber may contain a fiber comprising a synthetic fiber such as polyamide fibers, polyester fibers, polyolefin fibers etc.

The absorbent article of the present invention has a structure at which the above absorbent material is held between a liquid permeable sheet (top sheet) through which an aqueous liquid can pass and a liquid impermeable sheet (back sheet) through which an aqueous liquid can not pass. The liquid permeable sheet is arranged on a side contacting with a human body, while the liquid impermeable sheet is arranged on a side which is not contacted with a human body.

Examples of the liquid permeable sheet include nonwoven fabrics comprising polyethylene, polypropylene, polyester, or polyamide etc., a porous synthetic resin sheet and the like. Examples of the liquid impermeable sheet include a film comprising synthetic resins such as polyethylene, polypropylene, or polyvinylchloride etc.; a film comprising a composite material of these synthetic resins and these nonwoven fabrics, and the like, but the present invention is not limited to such the examples.

A size of the liquid permeable sheet and the liquid impermeable sheet can not be unconditionally determined because the size is different depending on use of the absorbent articles. Thus, it is preferable that such the size is appropriately adjusted depending on its use.

EXAMPLES

The present invention will be explained in more detail below on the basis of Examples, but the present invention is not limited to these Examples.

A. Production of Water-Absorbing Resin Particle

In Examples 1-5, a two-stage post-crosslinking process was performed according to a process for producing the water-absorbing resin particle of the present invention to obtain water-absorbing resin particles of the present invention.

In Comparative Examples 1-3, a water-absorbing resin particle for comparison was obtained by an one-stage post-crosslinking process.

Example 1

Step 1: Preparation of Water-Absorbing Resin Particle Precursor

To a five-necked cylindrical round-bottom flask of 2000 mL volume equipped with a stirrer, a refluxing condenser, a dropping funnel, a thermometer and a nitrogen gas inlet tube, were added 340 g of n-heptane and 0.92 g of sucrose fatty acid ester having HLB of 3.0 [manufactured by Mitsubishi-Kagaku Foods Corporation, trade name: S-370], the mixture was heated to 70° C. while being dispersed, to dissolve materials and this was then cooled to 55° C.

Separately, 92 g (1.02 moles) of a 80.5% by mass aqueous acrylic acid solution was added to a conical flask of 500 mL volume. To this flask was added 102.2 g (0.77 mole) of a 30% by mass aqueous sodium hydroxide solution dropwise while cooling externally, to neutralize 75 mole % of acrylic acid. Further, 50.2 g of water, 0.11 g (0.00041 mole) of potassium persulfate as a water-soluble radical polymerization initiator, and 8.3 mg (0.000047 mole) of ethylene glycol diglycidyl ether as a crosslinking agent were added to prepare an aqueous monomer solution for a first stage polymerization.

A total amount of this aqueous monomer solution for a first stage polymerization was added to the above five-necked cylindrical round-bottom flask while stirring to be dispersed, and the internal of the system was sufficiently replaced with a nitrogen gas, and then, a polymerization reaction was carried out for one hour while keeping a bath temperature at 70° C. The resultant slurry reaction mixture was then cooled to room temperature.

To another conical flask of 500 mL volume was added 119.1 g (1.32 moles) of a 80.5% by mass aqueous acrylic acid solution, and then 132.2 g (0.99 mole) of a 30% by mass aqueous sodium hydroxide solution was added to this flask dropwise to neutralize 75 mole % of acrylic acid while cooling externally. Further, 27.4 g of water and 0.14 g (0.00052 mole) of potassium persulfate were added thereto to prepare an aqueous monomer solution for a second stage polymerization, and this was cooled in an ice-water bath.

A total amount of the aqueous monomer solution for a second stage polymerization was added to the above resultant reaction mixture, the internal of the system was sufficiently replaced with a nitrogen gas again, and then a second stage polymerization reaction was carried out for 2 hours while keeping a bath temperature at 70° C.

After completion of the polymerization, the reaction mixture was heated in an oil bath at 120° C., only 234 g of water was removed out of the system by using azeotropic distillation to obtain a water-absorbing resin particle precursor. At this time, a remaining water amount of the water-absorbing resin particle precursor was 84 g, and a water content was 40% (a theoretical resin solid matter amount in this Example is 209 g).

Step 2: Production of Water-Absorbing Resin Particle

To the resultant water-absorbing resin particle precursor was added 4.22 g (0.00049 mole) of a 2% by mass aqueous ethylene glycol diglycidyl ether solution as a post-crosslinking agent, followed by mixing.

A first post-crosslinking reaction was carried out while heating the mixture in an oil bath at 120° C. and removing only water out of the system by using azeotropic distillation. At this time, 28 g of a water was removed and, thereby, a remaining water amount was 60 g and a water content was 29%.

Subsequently, 2.53 g (0.00029 mole) of a 2% by mass aqueous ethylene glycol diglycidyl ether solution as a post-crosslinking agent was added to the mixture, followed by mixing.

This mixture was heated in an oil bath at 120° C., and a water and n-heptane in the resultant gel material were removed by distillation, and then a second post-crosslinking reaction was carried out while drying the mixture to obtain 222.5 g of a water-absorbing resin particle having a mass mean particle diameter of 381 μm. In addition, a final water content (drying loss) of the water-absorbing resin particle was 5%.

Example 2

According to the same manner as that of Example 1 except that an addition amount of the 2% by mass aqueous ethylene glycol diglycidyl ether solutions, which is a post-crosslinking agent used in the first post-crosslinking reaction step, was changed to 2.11 g (0.00024 mole), an addition amount of the 2% by mass aqueous ethylene glycol diglycidyl ether solution, which is a post-crosslinking agent used in the second post-crosslinking reaction step, was changed to 2.11 g (0.00024 mole), and water contents in the first and second post-crosslinking steps were changed to 45% and 29%, respectively, in Example 1, 222.4 g of a water-absorbing resin particle having a mass mean particle diameter of 373 μm was obtained. In addition, a final water content (drying loss) of the water-absorbing resin particle was 4%.

Example 3

Step 1: Preparation of Water-Absorbing Resin Particle Precursor

To a five-necked cylindrical round-bottom flask of 2000 mL volume equipped with a stirrer, a refluxing condenser, a dropping funnel, a thermometer and a nitrogen gas inlet tube, were added 340 g of n-heptane and 0.92 g of sucrose fatty acid ester having HLB of 3.0 [manufactured by Mitsubishi-Kagaku Foods Corporation, trade name: S-370], the mixture was heated to 70° C. while being dispersed to dissolve the materials, and this was then cooled to 55° C.

Separately, 92 g (1.02 moles) of a 80.5% by mass aqueous acrylic acid solution was added to a conical flask of 500 mL volume. To this flask was added 102.2 g (0.77 mole) of a 30% by mass aqueous sodium hydroxide solution dropwise while cooling externally, to neutralize 75 mole % of acrylic acid. Further, 50.2 g of water, 0.11 g (0.00041 mole) of potassium persulfate as a water-soluble radical polymerization initiator, and 8.3 mg (0.000047 mole) of ethylene glycol diglycidyl ether as a crosslinking agent were added to prepare an aqueous monomer solution for a first stage polymerization.

A total amount of this aqueous monomer solution for a first stage polymerization was added to the above five-necked cylindrical round-bottom flask while stirring to be dispersed, and the internal of the system was sufficiently replaced with a nitrogen gas, and then a polymerization reaction was carried out for one hour while keeping a bath temperature at 70° C. The resultant slurry reaction mixture was then cooled to room temperature.

To another conical flask of 500 mL volume was added 119.1 g (1.32 moles) of a 80.5% by mass aqueous acrylic acid solution, and then 132.2 g (0.99 mole) of a 30% by mass aqueous sodium hydroxide solution was added to this flask dropwise to neutralize 75 mole % of acrylic acid while cooling externally. Further, 27.4 g of water, 0.14 g (0.00052 mole) of potassium persulfate and 0.54 g (0.0025 mole) of disodium phosphite pentahydrate were added thereto to prepare an aqueous monomer solution for a second stage polymerization, and this was cooled in an ice-water bath.

A total amount of the aqueous monomer solution for a second stage polymerization was added to the above resultant reaction mixture, the internal of the system was sufficiently replaced with a nitrogen gas again, and then a second stage of a polymerization reaction was carried out for 2 hours while keeping a bath temperature at 70° C.

After completion of the polymerization, the reaction mixture was heated in an oil bath at 120° C., and only 224 g of water was removed out of the system by using azeotropic distillation to obtain a water-absorbing resin particle precursor. At this time, a remaining water amount of the water-absorbing resin particle precursor was 94 g, and a water content was 45% (a theoretical resin solid matter amount in this Example is 209 g).

Step 2: Production of Water-Absorbing Resin Particle

To the resultant water-absorbing resin particle precursor was added 4.22 g (0.00049 mole) of a 2% by mass aqueous ethylene glycol diglycidyl ether solution as a post-crosslinking agent, followed by mixing.

A first post-crosslinking reaction was carried out while heating the mixture in an oil bath at 120° C. and removing only water out of the system by using azeotropic distillation. At this time, 36 g of a water was removed and, thereby, a remaining water amount was 62 g and a water content was 30%.

Subsequently, 1.48 g (0.00017 mole) of a 2% by mass aqueous ethylene glycol diglycidyl ether solution as a post-crosslinking agent was added to the mixture, followed by mixing.

This mixture was heated in an oil bath at 120° C., and a water and n-heptane in the resultant gel material were removed by distillation, and then a second post-crosslinking reaction was carried out while drying the mixture to obtain 223.1 g of a water-absorbing resin particle having a mass mean particle diameter of 380 μm. In addition, a final water content (drying loss) of the water-absorbing resin particle was 5%.

Example 4

According to the same manner as that of Example 3 except that the addition amount of the 2% by mass aqueous ethylene glycol diglycidyl ether solution, which is a post-crosslinking agent used in the first post-crosslinking reaction step, was changed to 6.33 g (0.00073 mole), an addition amount of a 2% by mass aqueous ethylene glycol diglycidyl ether solution, which is a post-crosslinking agent used in the second post-crosslinking reaction step, was changed to 0.53 g (0.000061 mole), and water contents in the first and second post-crosslinking steps were changed to 45% and 29%, respectively, in Example 3, 222.7 g of a water-absorbing resin particle having a mass mean particle diameter of 370 μm was obtained. In addition, a final water content (drying loss) of the water-absorbing resin particle was 5%.

Example 5

Step 1: Preparation of Water-Absorbing Resin Particle Precursor

To a five-necked cylindrical round-bottom flask of 2000 mL volume equipped with a stirrer, a refluxing condenser, a dropping funnel, a thermometer and a nitrogen gas inlet tube, were added 340 g of n-heptane and 0.92 g of sucrose fatty acid ester having HLB of 3.0 [manufactured by Mitsubishi-Kagaku Foods Corporation, trade name: S-370], the mixture was heated to 70° C. while being dispersed, to dissolve the materials and this was then cooled to 55° C.

Separately, 92 g (1.02 mole) of a 80.5% by mass aqueous acrylic acid solution was added to a conical flask of 500 mL volume. To this flask was added 102.2 g (0.77 mole) of a 30% by mass aqueous sodium hydroxide solution dropwise while cooling externally, to neutralize 75 mole % of acrylic acid. Further, 50.2 g of water, 0.11 g (0.00041 mole) of 2,2'-azobis (2-amidinopropane) dihydrochloride as a water-soluble radical polymerization initiator, and 8.3 mg (0.000047 mole) of ethylene glycol diglycidyl ether as a crosslinking agent were added to prepare an aqueous monomer solution for a first stage polymerization.

A total amount of this aqueous monomer solution for a first stage polymerization was added to the above five-necked cylindrical round-bottom flask while stirring to be dispersed, and the internal of the system was sufficiently replaced with a nitrogen gas, and then a polymerization reaction was carried out for one hour while keeping a bath temperature at 70° C. The resultant slurry reaction mixture was then cooled to room temperature.

To another conical flask of 500 mL volume was added 119.1 g (1.32 mole) of a 80.5% by mass aqueous acrylic acid solution, and then 132.2 g (0.99 mole) of a 30% by mass aqueous sodium hydroxide solution was added to this flask dropwise to neutralize 75 mole % of acrylic acid while cooling externally. Further, 27.4 g of water, 0.14 g (0.00052 mole) of 2,2'-azobis(2-amidinopropane) dihydrochloride and 10.7 mg (0.000061 mole) of ethylene glycol diglycidyl ether were added thereto to prepare an aqueous monomer solution for a second stage polymerization, and this was cooled in an ice-water bath.

A total amount of the aqueous monomer solution for a second stage polymerization was added to the above resultant reaction mixture, the internal of the system was sufficiently replaced with a nitrogen gas again, and then a second stage of a polymerization reaction was carried out for 2 hours while keeping a bath temperature at 70° C.

After completion of the polymerization, the reaction mixture was heated in an oil bath at 120° C., and only 224 g of water was removed out of the system by using azeotropic distillation to obtain a water-absorbing resin particle precursor. At this time, a remaining water amount of the water-absorbing resin particle precursor was 94 g, and a water content was 45% (a theoretical resin solid matter amount in this Example is 209 g).

Step 2: Production of Water-Absorbing Resin Particle

To the resultant water-absorbing resin particle precursor was added 4.22 g (0.00049 mole) of a 2% by mass aqueous ethylene glycol diglycidyl ether solution as a post-crosslinking agent, followed by mixing.

A first post-crosslinking reaction was carried out while heating the mixture in an oil bath at 120° C. and removing only water out of the system by using azeotropic distillation. At this time, 38 g of a water was removed and, thereby, a remaining water amount was 60 g and a water content was 29%.

Subsequently, 3.17 g (0.00036 mole) of a 2% by mass aqueous ethylene glycol diglycidyl ether solution as a post-crosslinking agent was added to the mixture, followed by mixing.

This mixture was heated an oil bath at 120° C., and a water and n-heptane in the resultant gel material were removed by distillation, and then a second post-crosslinking reaction was carried out while drying the mixture to obtain 223.7 g of a water-absorbing resin particle having a mass mean particle diameter of 378 µm. In addition, a final water content (drying loss) of the water-absorbing resin particle was 3%.

Comparative Example 1

Step 1: Preparation of Water-Absorbing Resin Particle Precursor

To a five-necked cylindrical round-bottom flask of 2000 mL volume equipped with a stirrer, a refluxing condenser, a dropping funnel, a thermometer and a nitrogen gas inlet tube, were added 340 g of n-heptane and 0.92 g of sucrose fatty acid ester having HLB of 3.0 [manufactured by Mitsubishi-Kagaku Foods Corporation, trade name: S-370], the mixture was heated to 70°C while being dissolve materials and this was then cooled to 55° C.

Separately, 92 g (1.02 moles) of a 80.5% by mass aqueous acrylic acid solution was added to a conical flask of 500 mL volume. To this flask was added 102.2 g (0.77 mole) of a 30% by mass aqueous sodium hydroxide solution dropwise while cooling externally, to neutralize 75 mole % of acrylic acid. Further, 50.2 g of water, 0.11 g (0.00041 mole) of potassium persulfate as a water-soluble radical polymerization initiator, and 8.3 mg (0.000047 mole) of ethylene glycol diglycidyl ether as a crosslinking agent were added to prepare an aqueous monomer solution for a first stage polymerization.

A total volume of this aqueous monomer solution for a first stage polymerization was added to the above five-necked cylindrical round-bottom flask while stirring to be dispersed, and the internal of the system was sufficiently replaced with a nitrogen gas, and then a polymerization reaction was carried out for one hour while keeping a bath temperature at 70° C. The resultant slurry reaction mixture was then cooled to room temperature.

To another conical flask of 500 mL volume was added 119.1 g (1.32 moles) of a 80.5% by mass aqueous acrylic acid solution, and then 132.2 g (0.99 mole) of a 30% by mass aqueous sodium hydroxide solution was added to this flask dropwise to neutralize 75 mole % of acrylic acid while cooling externally. Further, 27.4 g of water and 0.14 g (0.00052 mole) of potassium persulfate were added thereto to prepare an aqueous monomer solution for a second stage polymerization, and this was cooled in an ice-water bath.

A total amount of the aqueous monomer solution for a second stage polymerization was added to the above resultant reaction mixture, the internal of the system was sufficiently replaced with a nitrogen gas again, and then a second stage of polymerization reaction was carried out for 2 hours while keeping a bath temperature at 70° C.

After completion of the polymerization, the reaction mixture was heated in an oil bath at 120° C., only 224 g of water was removed out of the system by using azeotropic distillation to obtain a water-absorbing resin particle precursor. At this time, a remaining water amount of the water-absorbing resin particle precursor was 94 g, and a water content was 45% (a theoretical resin solid matter amount in this Example is 209 g).

Step 2: Production of Water-Absorbing Resin Particle

To the resultant water-absorbing resin particle precursor was added 3.70 g (0.00042 mole) of a 2% by mass aqueous ethylene glycol diglycidyl ether solution as a post-crosslinking agent, followed by mixing.

A first post-crosslinking reaction was carried out while heating the mixture in an oil bath at 120° C. and removing only water out of the system by using azeotropic distillation. At this time, 37 g of a water was removed and, thereby, a remaining water content was 60 g and a water content was 29%.

Subsequently, this mixture was heated in an oil bath at 120° C., and a water and n-heptane in the resultant gel material were removed by distillation, and dried to obtain 222.3 g of a water-absorbing resin particle having a mass mean particle diameter of 366 µm. In addition, a final water content (drying loss) of the water-absorbing resin particle was 5%.

Comparative Example 2

According to the same manner as that of Comparative Example 1 except that an addition amount of the 2% by mass aqueous ethylene glycol diglycidyl ether solution used in the post-crosslinking reaction step was changed to 7.81 g (0.00090 mole), the water content in the post-crosslinking reaction step was changed to 23%, and the subsequent azeotropic distillation was not carried out in Comparative Example 1, 222.2 g of a water-absorbing resin particle having a mass mean particle diameter of 374 µm was obtained. In addition, a final water content (drying loss) of the water-absorbing resin particle was 5%.

Comparative Example 3

According to the same manner as that of Example 3 except that the second post-crosslinking reaction was not carried out in Example 3, the first step of the post-crosslinking reaction, the azeotropic distillation and drying were carried out to obtain 222.8 g of a water-absorbing resin particle having a mass mean particle diameter of 373 µm. In addition, a final water content (drying loss) of the water-absorbing resin particle was 5%.

B. Evaluation of Properties of Water-Absorbing Resin Particle

For the water-absorbing resin particles of Examples 1-5 and Comparative Examples 1-3, (1) the water retention capacity, (2) the water-absorbing capacity, (3) a gel strength, (4) a water-soluble substance and (5) drying loss were measured by procedures below. Results are shown in Table 1.

(1) Physiological Saline Retention Capacity of Water-Absorbing Resin Particle

Each 2.0 g of water-absorbing resin particles were weighed in a cotton bag (Cottonbroad No. 60, width 100 mm×length 200 mm), and placed into a 500 mL-beaker. 500 g of Physiological saline (0.9% aqueous sodium chloride solution; the same hereinafter) was poured into the cotton bag at once, and the saline was dispersed so as not to generate an unswollen lump of the water-absorbing resin particles. An upper part of the cotton bag was tied up with a rubber band, and the cotton bag was allowed to stand for 1 hour, to sufficiently swell the water-absorbing resin particles. The cotton bag was dehydrated for 1 minute with a dehydrator (Kokusan Enshinki Co., Ltd., product number: H-122) set to have a centrifugal force of 167 G, and a mass Wa (g) of the cotton bag containing swollen gels after the dehydration was measured. The same procedures were carried out without adding water-absorbing resin particles, and an empty mass Wb (g) of the cotton bag upon wetting was measured. The water-retention capacity was calculated from the following equation:

Water-retention capacity $(g/g)=[Wa-Wb](g)$/mass of water absorbing resin particle (g)

(2) Physiological Saline Absorbing Capacity Under the Load of 4.14 kPa

The physiological saline absorbing capacity of water-absorbing resin particles under the load of 4.14 kPa was measured with a measuring apparatus 1 of which an outline constitution was shown in FIG. 1.

The measuring apparatus 1 shown in FIG. 1 comprises a burette part 11, an inlet tube 12, a measuring platform 13 and a measuring part 14 placed on the measuring platform 13.

The burette part 11 is connected to a rubber plug 115 at an upper part of a burette 111, and to an inhaled air inlet tube 113 and a cock 112 at a lower part of a burette 111, and the inhaled air inlet tube 113 has a cock 114 at a tip thereof.

An inlet tube 12 is attached between the burette part 11 and the measuring platform 13, and an internal diameter of the inlet tube 12 is 6 mm. There is a hole of a diameter of 2 mm at a center of the measuring platform 13 and the hole is connected with the inlet tube 12.

The measuring part 14 has a cylinder 141 made of an acrylate resin, a nylon mesh 142 adhered to the bottom of the cylinder 141, and a weighting 143. An internal diameter of the cylinder 141 is 20 mm. An opening of the nylon mesh 142 is 75 μm (200 mesh). During the measurement, the water-absorbing particles 2 are uniformly sprinkled on the nylon mesh 142.

The weighting 143 has an internal diameter of 19 mm and a mass of 119.6 g. The weighting is placed on the water-absorbing resin particles 2, and is constructed such that the weighting can add the load of 4.14 kPa to the water-absorbing resin particles 2.

And then the measurement procedures are explained below. The measurement is carried out in a room at 25° C.

Firstly, the cock 112 and the cock 114 of the burette part 11 are closed, a 0.9% by mass aqueous sodium chloride solution regulated at 25° C. is placed in the apparatus from an upper part of the burette 111, the upper part of the burette is plugged with the rubber plug 115, and then the cock 112 and the cock 114 of the burette part 11 are opened.

A height of the measuring platform 13 is then adjusted such that a surface level of a 0.9% by mass aqueous sodium chloride solution provided from the opening of the inlet tube of a center of the measurement platform 13, has the same level as a height of the upper surface of the measurement platform 13.

Separately, the measuring part 14 is made ready by uniformly sparging 0.10 g of the water-absorbing resin particles 2 on the nylon mesh 142 of the cylinder 141, and placing the weighting 143 on the water-absorbing resin particles 2. The measuring part 14 is then placed such that its center corresponds to the opening of the inlet tube placed on a center of the measuring part 13.

After 60 minutes have passed from a time point at which bubbles began to be generated in the burette 111 from the inhaled air inlet tube 113, and the water-absorbing resin particles 2 began to absorb water, a decreased amount Wc (ml) of a 0.9% by mass aqueous sodium chloride solution (i.e., an amount of a 0.9% by mass aqueous sodium chloride solution absorbed by the water-absorbing resin particles 2) is read.

Figure 2:
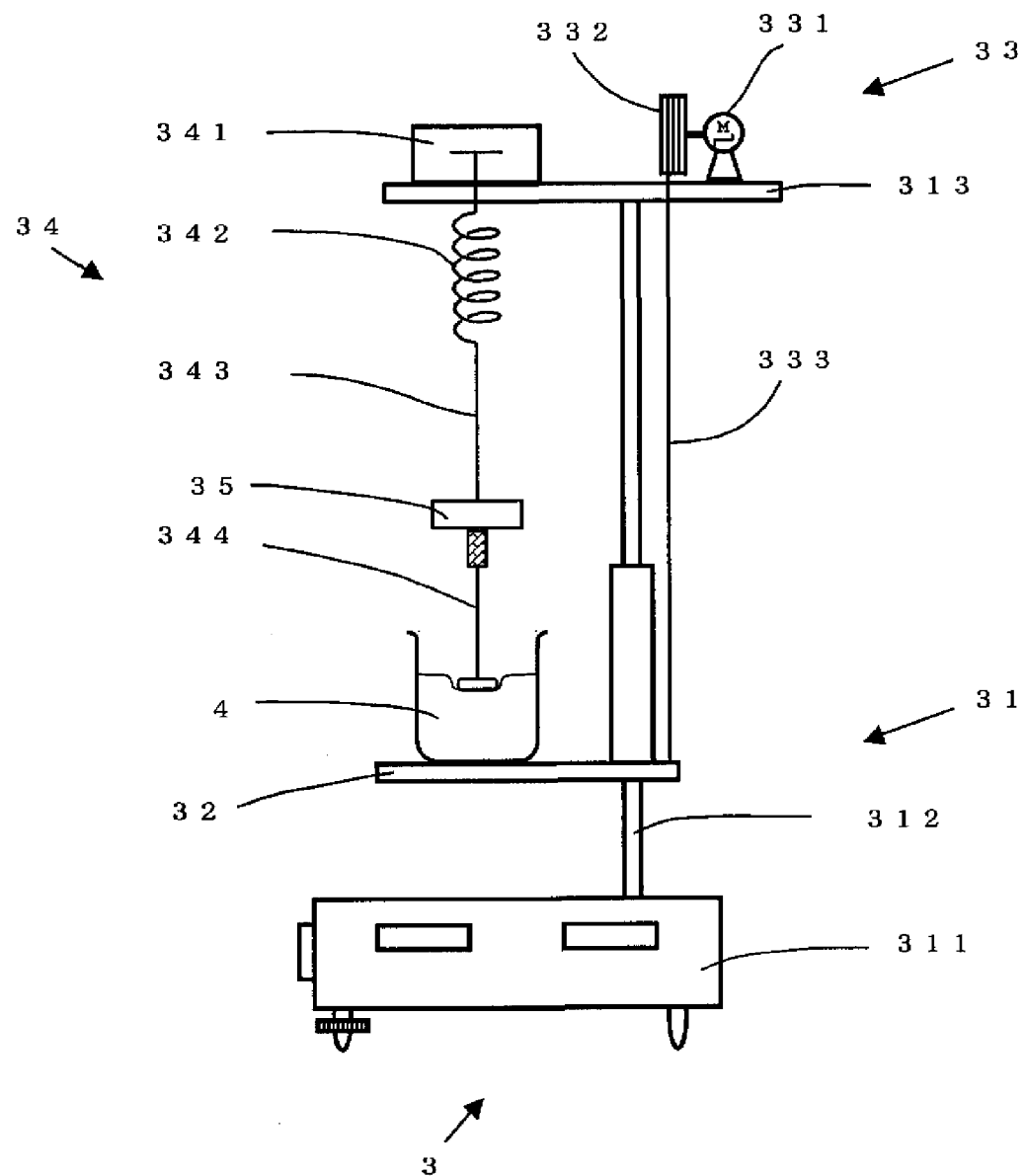
[FIG. 2] Schematic diagram of an apparatus for measuring a gel strength of water-absorbing resin particles.

The physiological saline absorbing capacity of the water-absorbing resin particles 2 under the load of 4.14 kPa was calculated by the following equation:

Physiological saline absorbing capacity of water-absorbing resin particles under the load of 4.14 kPa $(ml/g)=Wc/0.10$ (3) Gel Strength of Water-Absorbing Resin Particle A gel strength in the present invention is a value of the following gel, measured with an equipment 3 (e.g., Neocardmeter manufactured by Iio Electronics, Product No. M-303) having the measurement principle as shown in FIG. 2.

The equipment 3 is composed of a support 31, a movable plate 32 for mounting a measurement sample (gel) 4 thereon, a driving part 33 for driving the movable plate 32, and a measurement part 34.

In the support 31, a counter 313 is fixed at an upper part of a pole 312 stood on a supporting plate 311. The movable plate 32 is attached to the pole 312 so that the movable plate 32 can move up and down. A pulse motor 331 is mounted on the counter 313 and, by rotating a pulley 332, the movable plate 32 is moved up and down via wire 333.

In the measurement part 34, a load cell 341 for measuring a distortion caused by deformation is equipped via a precision spring 342 and a connecting axis 343 with a pressure sensitive axis 344 with a disk. A diameter of the disk can vary depending on the measurement conditions. An upper part of the pressure sensitive axis 344 with a disk can be mounted with a weight 35.

The working principle of the equipment 3 is as follows:

The precision spring 342 is fixed at the load cell 341 (stress detector) above the precision spring, and the pressure sensitive axis 344 with a disk is connected to the precision spring below the precision spring, and they are vertically hanged with a predetermined weighting 35. The movable plate 32 on which a measurement sample 4 is placed is elevated at a constant speed by rotation of the pulse motor 331. A constant speed load is applied to the sample 4 via the spring 342, and a distortion caused by deformation is measured with the load cell 341 and then a hardness is computed by the measurement.

Into a beaker of a volume of 100 mL was weighed 49.0 g of physiological saline and a magnetic stirrer bar (8 mm φ×30 mm, ringless) was placed therein, and the beaker was arranged on a magnetic stirrer (manufactured Iuchi Corporation, HS-30D). Subsequently, the magnetic stirrer bar was adjusted so as to rotate at 600 rpm, and a bottom of a vortex caused by rotation of the magnetic stirrer bar was adjusted so as to be near an upper part of the magnetic stirrer bar.

Then, 11.0 g of the water-absorbing resin particles was placed into the beaker with stirring, the stirring was continued until a rolling vortex disappeared to make a liquid level horizontal and, thereby, a gel to be the measurement sample 4 was prepared.

After one hour, a hardness value of the gel was measured with the equipment 3 (Neocardmeter manufactured by Iio Electronics, Product No. M-303, the setting: disk of the pressure sensitive axis 16 mm φ, the load 100 g, speed 7 sec/inch and viscous mode). A gel strength was calculated from the resultant hardness value (dyne/cm$^2$) by the following equation:

Gel strength (Pa)=[hardness value]×0.1 wherein 0.1: coefficient for converting units (from dyne/$cm^2$ to Pa)

(4) Water-Soluble Substance of Water-Absorbing Resin Particle

Into a beaker of a volume of 500 mL was weighed 500 g of physiological saline, and a magnetic stirrer bar (8=mm φ×30 mm, ringless) was placed therein, and the beaker was arranged on a magnetic stirrer (manufactured Iuchi Corporation, HS-30D). Subsequently, the magnetic stirrer bar was adjusted so as to rotate at 600 rpm, and a bottom of a vortex caused by rotation of the magnetic stirrer bar was adjusted so as to be near an upper part of the magnetic stirrer bar.

Then, 2.0 g of the water-absorbing resin particles was rapidly poured between a center of a vortex in the beaker and a side face of the beaker, and dispersed, and stirred for 3 hours. Water with the water-absorbing resin particles dispersed therein after 3 hours stirring was filtrated with a JIS standard sieve (opening 75 μm), and the resultant filtrate was further suction-filtrated using Kiriyama-type funnel (Filter paper No. 6).

Into a beaker of a volume of 100 ml which had been dried at 140° C. until a constant weight and cooled to room temperature in advance was weighted 80±0.01 g the resulting filtrate, this was dried until a constant weight with a hot air drying device (manufactured by ADVANTEC Corporation) having an internal temperature set at 140° C., and then a mass Wd (g) of a filtrate solid matter was measured.

On the other hand, according to the same manner as the above procedure without using water-absorbing resin particles, a blank mass We (g) was measured, and a water-soluble substance was calculated by the following equation:

Water-soluble substance (% by mass)=[($Wd-We$)× (500/80)]/2×100

(5) Drying Loss of Water-Absorbing Resin Particle

Into a previously weighted aluminum foil case (No. 8) was precisely weighed 2 g of water-absorbing resin particles (Wf (g)). The sample was dried for 2 hours with a hot air drying device (manufactured by ADVANTEC Corporation) having an internal temperature set at 105° C., allowed to cool in a desiccator, and then a mass Wg (g) of the water-absorbing resin particles after drying was measured. Drying loss of water-absorbing resin particles was calculated by the following equation:

Drying loss (%)=[$Wf-Wg$]/$Wf$×100

TABLE 1

| | Physiological saline retention capacity (g/g) | Physiological saline absorbing capacity under the load of 4.14 kPa (ml/g)) | Gel strength (Pa) | Water soluble substance (% by mass) |
|---|---|---|---|---|
| Example 1 | 42 | 21 | 1940 | 7 |
| Example 2 | 45 | 16 | 1720 | 8 |
| Example 3 | 43 | 23 | 2040 | 8 |
| Example 4 | 47 | 18 | 1780 | 9 |
| Example 5 | 52 | 16 | 1210 | 12 |
| Comparative Example 1 | 45 | 10 | 780 | 13 |
| Comparative Example 2 | 46 | 8 | 420 | 30 |
| Comparative Example 3 | 48 | 9 | 280 | 16 |

The results of Table 1 show that the water-absorbing resin particles obtained by carrying out the two-stage post-crosslinking reaction according to the procedures of Examples 1-5, all possess the higher physiological saline absorbing capacity under the load, a higher gel strength, and a lower water-soluble substance even within a range of the higher water retention capacity of physiological saline, as compared with those obtained by carrying out the first post-crosslinking reaction according to the procedures of Comparative Examples 1-3, and that the particles are thus excellent as water-absorbing resin particles.

C. Production of Absorbent Articles

Example 6

Ten grams of the water-absorbing resin particles produced in Example 1 and 10 g of crushed wood pulps were dry-mixed, the mixture was blown onto a tissue paper having a size of 40 cm×12 cm and a weight of 1 g, another tissue paper having the same size and weight as the above paper was overlaid hereon to form a sheet, and a the load of 196 kPa was applied to press a whole sheet for 30 seconds to obtain an absorbent material. The resultant absorbent material was held with a polyethylene air-through nonwoven fabric having a basis weight of 20 g/$m^2$ and a polyethylene sheet to obtain an absorbent article.

Examples 7-10 and Comparative Examples 4-6

According to the same manner as that of Example 6 except that the water-absorbing resin particles obtained in each of Examples 2-5 and Comparative Examples 1-3 substituted for those produced in Example 1 were used in Example 6, absorbent articles were produced, and then the resultant absorbent articles were successively designated as absorbent articles of Examples 7-10 and Comparative Examples 4-6.

D. Evaluation of Properties of Water-Absorbing Article

Water absorbing articles of Examples 6-10 and Comparative Examples 4-6 were tested under two kinds of conditions by the following procedure.

Water-absorbing articles obtained in each Example and each Comparative Example were evaluated based on the following method. The results are shown in Table 2.

(6) Absorbent Article Test A

Preparation of Artificial Urine:

A suitable amount of distilled water was placed into a container of a volume of 10 L, and 60 g of sodium chloride, 1.8 g of calcium chloride dihydrate and 3.6 g of magnesium chloride hexahydrate were added thereto to dissolve materials. Then, 0.02 g of polyoxyethylene nonyl phenyl ether was added, and distilled water was further added thereto to a total mass to 6000 g.

Further, the solution was colored with a small amount of Food Blue No. 1 to prepare an artificial urine.

Measurement of permeation rate and flow-back:

A cylinder for liquid introduction having an inner diameter of 3 cm was placed at a center of an absorbent article, 50 ml of the artificial urine was introduced at once and, at the same time, a stopwatch was made to start. A time from introduction initiation to complete absorption of the liquid into the absorbent article was measured, and designated as a first permeation rate (seconds). The same procedures were then carried out after 30 and 60 minutes to measure second and third permeation rates (seconds). After 120 minutes from the first liquid introduction initiation, 50 g of a 10 cm×10 cm filter paper was placed on and near a liquid introductory point, and the load of 5.0 kg was applied thereto for 5 minutes. A mass of the filter paper after load application was measured, and a mass of the filter paper before load application was subtracted therefrom to obtain a flow-back amount (g).

(7) Absorbent Article Test B

The procedure was carried out according to the same manner as that of Absorbent Article Test A except that the number of liquid introduction was one time, an amount of the artificial urine was 150 ml, and loading was initiated 5 minutes after first introduction initiation.

TABLE 2

|  | Absorbent Article Test A | | | | Absorbent Article Test B | |
| --- | --- | --- | --- | --- | --- | --- |
|  | Permeation rate (seconds) | | | Amount of flow-back | Permeation rate | Amount of flow-back |
|  | 1st | 2nd | 3rd | (g) | (seconds) | (g) |
| Example 6 | 20 | 18 | 19 | 2.8 | 51 | 1.2 |
| Example 7 | 21 | 17 | 20 | 3.0 | 56 | 0.8 |
| Example 8 | 19 | 19 | 22 | 2.4 | 58 | 0.5 |
| Example 9 | 20 | 18 | 24 | 2.0 | 58 | 0.4 |
| Example 10 | 24 | 20 | 22 | 2.3 | 61 | 0.3 |
| Comparative Example 4 | 21 | 24 | 38 | 28.9 | 66 | 4.4 |
| Comparative Example 5 | 22 | 20 | 29 | 32.3 | 68 | 6.5 |
| Comparative Example 6 | 23 | 23 | 35 | 21.6 | 75 | 5.8 |

The results of Table 2 show that the absorbent articles of Examples 6-10 possess a sufficiently high permeation rate, and a smaller flow-back amount, and exert the stable and excellent performance as an absorbent article, as compared with those of Comparative Examples 4-6.

The invention claimed is:

1. A process for producing a water-absorbing resin particle, comprising a step of adding a post-crosslinking agent in at least two stages to a water-absorbing resin particle precursor obtained by polymerzing a water-soluble ethylenic unsaturated monomer to carry out a post-crosslinking reaction; wherein the process comprises:
a first post-crosslinking reaction step of adding a post-crosslinking agent to a water-absorbing resin particle precursor having a water content of not less than 35% to carry out a post-crosslinking reaction;
a water content adjustment step of reducing a water content of the post-crosslinked water-absorbing resin particle precursor to not less than 15% and less than 35%; and
a second post-crosslinking reaction step of adding a post-crosslinking agent to the post-crosslinked water-absorbing resin particle precursor having a reduced water content to carry out a post-crosslinking reaction.

2. The process for producing a water-absorbing resin particle according to claim 1, wherein the post-crosslinking agent is a glycidyl compound.

3. The process for producing a water-absorbing resin particle according to claim 1, wherein an addition amount of the post-crosslinking agent is 0.000005-0.002 mole in the first post-crosslinking reaction step, and 0.000005-0.001 mole in the second post-crosslinking reaction step, based on a total amount of 1 mole of the water soluble ethylenic unsaturated monomer used for obtaining the water-absorbing resin particle precursor.

4. A water-absorbing resin particle obtainable by the process according to claim 1, wherein the water-absorbing resin particle has a physiological saline retention capacity of 40-60 g/g, a physiological saline absorbing capacity under the load of 4.14 kPa of not less than 15 ml/g, a gel strength of not less than 500 Pa, and a water-soluble substance of not more than 15% by mass.

5. An absorbent material comprising a water-absorbing resin particle as defined in claim 4 and a hydrophilic fiber.

6. An absorbent article comprising the absorbent material as defined in claim 5 held between a liquid permeable sheet and a liquid impermeable sheet.

* * * * *